(12) United States Patent
Selker (10) Patent No.: US 6,450,954 B1
(45) Date of Patent: Sep. 17, 2002

(54) METHOD OF RANDOMIZING PATIENTS IN A CLINICAL TRIAL

(75) Inventor: Harry P. Selker, Wellesley, MA (US)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 09/431,750

(22) Filed: Nov. 1, 1999

(51) Int. Cl.$^7$ .................................................. A61B 5/00
(52) U.S. Cl. ........................ 600/300; 128/920; 128/925; 205/3
(58) Field of Search ................................ 600/300–301; 128/920–925; 705/2–3

(56) References Cited

U.S. PATENT DOCUMENTS

| | | |
|---|---|---|
| 4,457,315 A | 7/1984 | Bennish |
| 4,679,144 A | 7/1987 | Cox et al. |
| 4,998,535 A | 3/1991 | Selker et al. |

OTHER PUBLICATIONS

Brooks, Maria, "Predictors of Mortality and Mortality from Cardiac Causes in the Bypass Angioplasty Revascularization Investigation (BARI) Randomized Trial and Registry", American Heart Association, Inc., Jan. 4, 2000, pp. 2682–2689.

Brooks et al., Predictors of Mortality and Mortality From Cardiac Causes in the Bypass Angioplasty Revascularization Investigation (BARI) Randomized Trial and Registry, American Heart Association, Inc., Jan. 4, 2000, pp. 2682–2689.*

\* cited by examiner

Primary Examiner—Kevin Shaver
Assistant Examiner—Michael Astorino
(74) Attorney, Agent, or Firm—Fish & Richardson P.C.

(57) ABSTRACT

A randomization mechanism for enabling randomization of a patient to one of two treatment options having different time-to-treatments is presented. Data is received for a patient experiencing symptoms of the type treatable by either of the two treatment options. The received data is used to compute for a first treatment option of the two treatment options at its associated time-to-treatment a benefit value. Assuming a benefit value for the second treatment option is an estimate of the computed first benefit value, the received data and computed benefit value are used to compute a maximum allowable delay time during which the benefit value for the second treatment option is no less than the benefit value computed for the first treatment option. When provided a given delay time by which the time-to-treatment of the second treatment option lags the first treatment option time-to-treatment, the mechanism determines if the given delay time is less than or equal to the allowable delay time. If the given delay time is determined to be less than or equal to the allowable delay time, then the patient is eligible for randomization.

17 Claims, 10 Drawing Sheets

FIG. 1

Thrombolytic Predictive Instruments: 30-Day Mortality Component Predictive Instrument

Variable Coefficients

| Variable | Coefficient | P Value |
|---|---|---|
| Patient age | 0.0557 | <0.001 |
| Systolic blood pressure | | |
|    Patients with anterior or posterior acute myocardial infarction | -0.0277 | <0.001 |
|    Patients without anterior or posterior acute myocardial infarction | -0.0080 | |
| History of diabetes | 0.9215 | <0.001 |
| Heart rate | 0.0271 | <0.001 |
| ST-segment elevation (echocardiogram size of acute myocardial infarction) | 0.0424 | 0.0020 |
| Q waves without ST-segment elevation in inferior acute myocardial infarction | 0.3184 | 0.0383 |
| Acute myocardial infarction location (anterior or posterior acute myocardial infarction) | 3.6240 | <0.001 |
| Right bundle-branch block | 0.5763 | 0.0805 |
| Time from symptom onset to emergency department electrocardiogram | -0.1407 | 0.0448 |
| Impact of use of thrombolytic therapy | -1.2097 | 0.0097 |
| Intercept | -5.6340 | |

FIG. 2

Calculation for Sample patient Using the Thrombolytic Predictive Instrument 30-Day Mortality Component Predictive Instrument

| Patient Information Required for Model | Value for Patient | Variable Definition | Derived Value ($x$) | Regression Coefficient ($\beta$) | Product ($\beta \cdot x$) |
|---|---|---|---|---|---|
| Patient age | 57 years | If age >40 years and <60 years, then $x$ = age | 57 | 0.0557 | 3.1749 |
| Initial systolic blood pressure | 156 mm Hg | If anterior ST-segment elevation and systolic blood pressure >60, then $x$ = systolic blood pressure | 156 | -0.0277 | -4.3212 |
| History of diabetes | Yes | If history of diabetes present, then $x$ = 1 | 1 | 0.9215 | 0.9215 |
| Heart rate | 60 beats/min | If heart rate ≥ 0 beats/min and <70 beats/min, then $x$ = 0 | 0 | 0.00271 | 0.0000 |
| Amount of ST-segment elevation | 5.6 | $x$ = number of leads with ST-segment elevation – sum of ST-segment elevation in these leads | 9.6 | 0.0424 | 0.4070 |
| Leads with abnormal Q-wave and no ST-segement elevation | 1 | If anterior ST-segment elevation, then $x$ = 0 | 0 | 0.3184 | 0.0000 |
| Anterior infarction or posterior acute Myocardial infarction | Yes | If anterior ST-segment elevation, then $x$ = 1 | 1 | 3.6240 | 3.6240 |
| Presence or right bundle-branch block | None | If no right bundle-branch block is present, then $x$ = 0 | 0 | 0.5763 | 0.0000 |
| Time from symptom onset to Electrocardiogram (TONSET) | 2 hours | If not given thrombolytic therapy | 3 | -0.1407 | -0.4221* |
|  |  | If TONSET > 2 hours and ≤ 3 hours, then $x$ = 1.50 x TONSET |  |  |  |
|  |  | If given thrombolytic therapy, then $x$ = 6.25 |  |  | -0.8794* |
| Leads with ST-segment elevation | 4 | Earliness index = (number of leads with tall T waves + 0.5 x leads with ST-segment elevation without abnormal Q waves)/ number of leads with ST-segment elevation | 6.25 0.50 | -0.1407 — |  |
| With tall T waves | 0 |  |  |  |  |
| No abnormal Q waves | 4 |  |  |  |  |
| Impact of use of thrombolytic therapy Time to treatment | 3 hours | $x$ = (1 – time to treatment/9 x Earliness index | 0.33 | -1.2097 | -0.4032* |
| Model intercept |  |  | 1 | -5.6340 | -5.6340 |
| Sum of weighted patient-specific values without thrombolytic therapy = $\Sigma \beta x$ = |  |  |  |  | 2.2499 |
| Sum of weighted patient-specific values with thrombolytic therapy = $\Sigma \beta x$ = |  |  |  |  | -3.1104 |

Include only in sum for probability without thrombolytic therapy.
Include only in sum for probability with thrombolytic therapy.

Probability of 30-day mortality without thrombolytic therapy = $\dfrac{1}{1-\exp(\Sigma \beta x)} = \dfrac{1}{1-\exp(2.2499)} = 0.095$ Probability of 30-day mortality with thrombolytic therapy = $\dfrac{1}{1-\exp(\Sigma \beta x)} = \dfrac{1}{1-\exp(3.1104)} = 0.043$

METHOD OF RANDOMIZING PATIENTS IN A CLINICAL TRIAL

BACKGROUND OF THE INVENTION

The present invention relates generally to predictive instruments for computing a probability of a medical outcome.

One important application of statistical methods to medicine is the evaluation of the efficacy of treating diseases, and the use of statistical models to determine the likelihood of a particular patient's response to a treatment regimen. Some statistical methods include the use of so-called regression models that relate clinical variables gathered from patients being treated for a disease with the probable treatment outcomes of those patients. Logistic regression models are used to estimate the probability of defined outcomes as impacted by associated information.

A number of predictive instruments have been developed to use logistic regression equations to model the probability of mortality for a patient suffering from an acute cardiac condition. The probability of mortality refers to the probability of imminent death for the patient. That is, it is a short term, as opposed to a long term, probability of mortality which does not necessarily have a precisely defined period of time associated with it. One such predictive instrument for determining the probability of mortality of a cardiac patient is described in U.S. Pat. No. 4,957,115 to Dr. Harry P. Selker. Another predictive instrument, described in U.S. Pat. No. 4,998,535, evaluates the efficacy of administering a particular treatment—thrombolytic therapy (TT)—to a patient with a heart condition by comparing a computed first probability of mortality for the patient assuming that thrombolytic therapy is not administered and a second computed probability of mortality for the patient assuming that thrombolytic therapy is administered.

Acute myocardial infarction (AMI) is one of the most common causes of death in the United States. Therefore, the outcomes of its treatment and optimal care setting are of the. upmost importance. It is well understood that re-establishing coronary perfusion at the earliest possible time is a critical part of treatment. There are two general modes of coronary "reperfusion therapy": 1) thrombolytic therapy (TT); and 2) percutaneous transluminal coronary angioplasty(PTCA). TT can be given by any emergency department or physician in either a hospital or field setting. In contrast, PTCA requires a trained interventional cardiologist in a specialized setting with surgical support in the event of a complication.

Although TT remains the standard of care in reperfusion treatment for AMI, limited clinical studies suggest that PTCA may be substantially superior to TT in reducing mortality, at least in certain settings such as high-volume primary PTCA cardiac centers. To properly test the efficacy of PTCA, a more comprehensive PTCA effectiveness trial is performed. Such a trial could involve the random assignment of patients to either a local community hospital or to referral cardiac center. That is, some patients would be sent to a local hospital, while others would be transferred from the local hospital to a regional care center or the local hospital would be by-passed in favor of the regional cardiac center. In either case, there would be a delay associated with the extra time required to transport the patient beyond the local hospital (where care is readily available) to the more distant cardiac care center. Since time from the onset of AMI until treatment is a crucial determinant of medical outcome regardless of the reperfusion strategy employed, bypassing nearby community hospitals in favor of cardiac centers is not without risk. Thus, randomization under such conditions may be problematic.

SUMMARY OF THE INVENTION

In one aspect of the invention, to determine if a patient may be randomized to a treatment option, data are received for a patient experiencing symptoms of the type that may be treated by either of two treatment options including a first treatment option and a second treatment option. The first treatment option has an associated first time-to-treatment and the second treatment option has an associated second time-to-treatment that is greater than the first time-to-treatment by a given delay time. The second treatment option is estimated to be more effective than the first treatment option. The received data are used to compute a benefit value for the first treatment option at the first time-to-treatment. The received data and the computed benefit value associated with the first treatment option are used to compute for the second treatment option an allowable delay time during which a second benefit value for the second treatment option is no less than the first benefit value. Randomization information is produced based on the computed allowable delay time. The randomization information indicates whether or not the patient may be randomized to one of the two treatment options.

Embodiments of the invention may include one or more of the following features.

The first treatment option can be thrombolytic therapy (TT) and the second treatment option can be percutaneous transluminal coronary angioplasty (PTCA).

The first treatment option may be available at a local hospital and the second treatment option may be available at a more distant treatment center. The given delay time may correspond to the additional time required to transport a patient to the more distant treatment center.

The randomization information can be produced by determining if the given delay time is less than or equal to the allowable delay time and indicating that the patient may be randomly allocated to either the first or the second treatment option if the given delay time is determined to be less than or equal to the allowable delay time.

The randomization information can be produced by sending the computed allowable delay time to an output device for display.

In another aspect of the invention, benefit values are computed for the treatment options and confidence intervals associated with the computed benefit values are used to determine when randomization may occur. An overlap of the confidence intervals indicates that randomization is permissible.

In yet another aspect of the invention, probability of medical outcome values are computed for the first and second treatment option. A determination is made as to whether or not the computed probability of medical outcome values are equal. If equal, an indication that the patient may be randomly allocated to either the first or the second treatment option is provided.

The randomization mechanism of the present invention offers several advantages. It better enables clinicians to make critical treatment decisions involving trade-offs between the proximity of a cardiac center and the benefits associated with the care provided by such a cardiac center. Therefore, it provides for the use of randomization techniques when a delay in time-to-treatment has a critical impact on medical outcome for a patient. The randomization process can be used in clinical trials to further develop models for alternative treatment therapies such as PTCA. In addition, the randomization process can serve as an on-site decision aid for treatment of patients with AMI. As an on-site decision aid, it can be used by EMS providers and hospital emergency room physicians alike to predict which patients are likely to obtain the most incremental benefit from PTCA and to optimize the delivery of acute cardiac services. While the process is advantageous in applications in which time is a critical factor, it may be useful in clinical trials in general. For instance, it could applied in the administration of an on-location clinical trial, e.g., experimential drug testing.

BRIEF DESCRIPTION OF THE DRAWINGS

The above features and advantages of the present invention will become more apparent from the following detailed description taken in conjunction with the accompanying drawings, in which:

FIG. 3 is a predicted probability of mortality computation for a sample patient to be treated by TT;

DESCRIPTION OF THE PREFERRED EMBODIMENT

Figure 1:
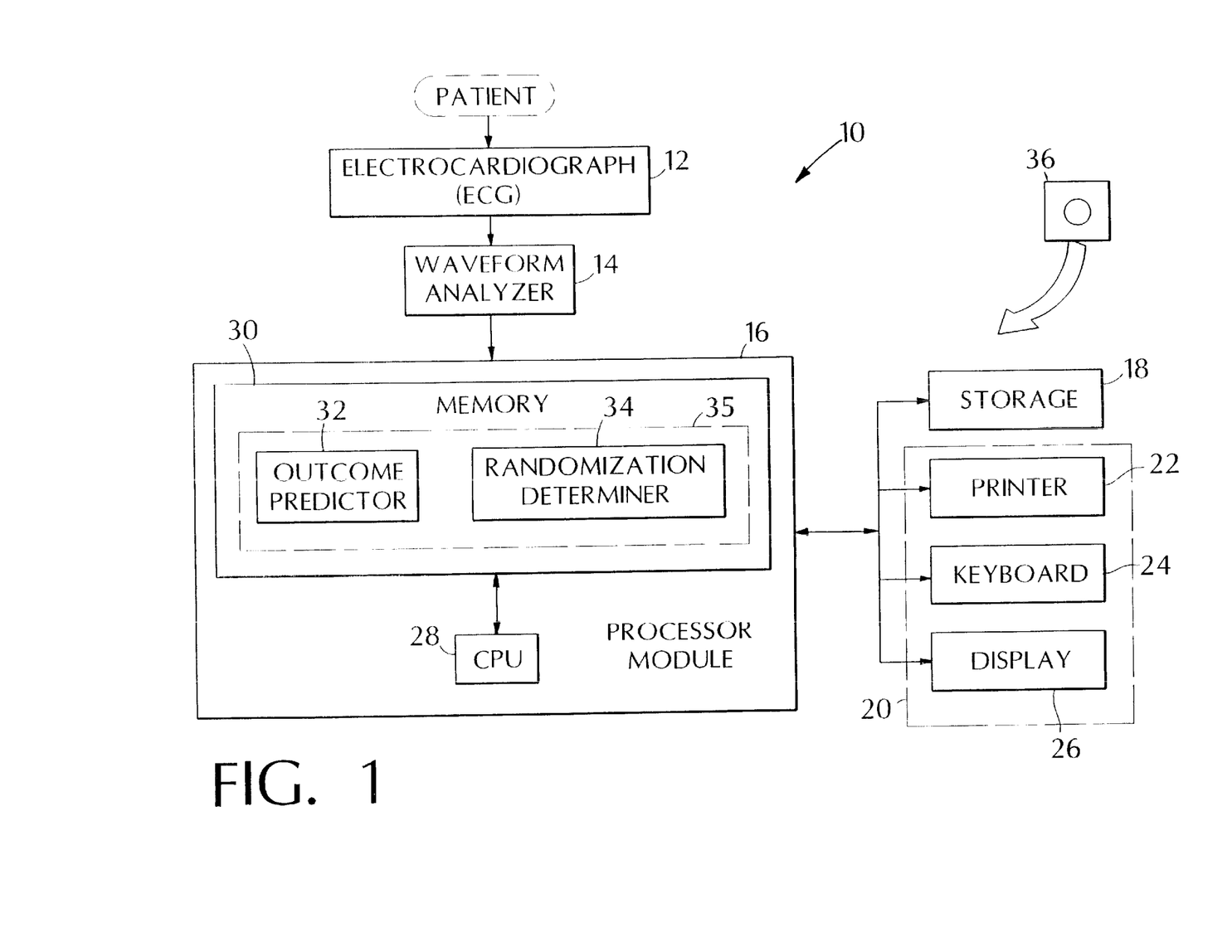
FIG. 1 is a block diagram of a predictive instrument for supporting a patient randomization process.

Referring to FIG. 1, a predictive instrument 10 which assists clinicians in determining if a particular patient is a suitable candidate for "randomization", i.e., random allocation of a patient to one of at least two available treatment options, typically occuring in a clinical trial setting. The predictive instrument 10 includes a patient monitoring device 12, an analyzer 14 for analyzing the output of the patient monitoring device 12 and a processor module 16. In the illustrated embodiment, the patient monitoring device 12 is an electrocardiograph and the analyzer 14 is a waveform analyzer. The electrocardiograph 12 monitors the cardiac activity of a patient (shown in dashed lines) who has recently experienced an acute myocardial infarction (AMI) and produces a set of ECG waveforms for that patient. The waveform analyzer 14 analyzes the ECG waveforms and recognizes the presence of certain characteristics that are particularly indicative of the cardiac condition of the patient, e.g., the presence and elevation or depression of S-T segments, the presence of Q waves, and the presence of elevated, depressed or inverted T-waves. The particular characteristics which the waveform analyzer recognizes depends upon the function that is performed by the predictive instrument which in turn determines the set of clinical variables that are required to perform that function.

The predictive instrument 10 further includes a mass storage device 18 (e.g., hard disk) and peripheral I/O devices 20, each of which is connected to the processor module 16. The peripheral I/O devices include a printer 22, an input device (e.g., keyboard) 24 and a display 26.

Still referring to FIG. 1, the processor module 16 receives the output of the waveform analyzer 14 in conjunction with other information about the patient that has been entered by a physician or medical care provider through the input device 24. The other information may include clinical data derived from the patient (e.g., systolic blood pressure, heart rate) as well as information relating to the patient's medical history (e.g., age, sex, previous history of AMI). The processor module 16 includes a CPU 28 operatively coupled to an internal memory 30 (e.g., RAM and/or ROM). Installed on the processor module 16 in the memory 30 is an outcome predictor 32 and a randomization determiner 34, or collectively, a patient randomization process 35. Both the outcome predictor 32 and the randomization determiner 34 are software processes which are executed by the CPU 28. The outcome predictor 32 uses some or all of the information sent by the waveform analyzer 14 and the input device 24 to compute probability of mortality values for thrombolytic therapy (TT) and percutaneous transluminal coronary angioplasty (PTCA), as will be described later. The randomization determiner 34 produces randomization-related information based on the computed probability of mortality values, also described below.

Still referring to FIG. 1, the results from the patient randomization process 35 are output to the display 26 and/or the printer 22. The outcome predictor 32 and randomization determiner 34 may be implemented as a single software program or separate software programs, typically presented on a removable, computer-readable medium, e.g., a CD-ROM or floppy disk 36, and downloaded into the memory 30 for subsequent execution by the CPU 28 of the processor module 16. Alternatively, the program or programs may be loaded into the mass storage device 18.

Though shown as separate units, the electrocardiograph 12 and the waveform analyzer 14 are commercially available as a single unit. For example, Hewlett Packard makes the HP Pagewriter XLi which is a computer-assisted ECG unit. The unit includes an internal computer that can be programmed to perform waveform analysis as well as identify the location of a myocardial infarction based on the characteristics of the set of signals produced by the monitoring leads of the ECG. In addition to performing the above-mentioned wave analysis functions, the unit's computer can perform the functions of other components within the predictor instrument, such as the outcome predictor 32 and randomization determiner 34 processes.

Generally, the randomization process 35 (FIG. 1) is used to assist medical care providers in identifying which patients can be randomized to one of at least two treatment options, either for clinical trial or clinical decision-making purposes. One important factor that has a significant impact on a medical care provider's ability to randomize between two treatment options is time-to-treatment. Specifically, time-to-treatment (as used herein) refers to the period of time from onset of symptoms to treatment. For a specific patient, then, each treatment option has an associated time-to-treatment. That time-to-treatment may include a transport time, which is particularly critical in emergency cardiac care situations. If a first treatment option such as TT is available at a local hospital and an alternative second treatment option such as PTCA is available at a more distant treatment center, treatment by PTCA would be delayed by a time corresponding to the additional time required to transport a patient to a more distant treatment center. Thus, the randomization process examines, for a particular patient, the impact of that time delay on the predicted benefit for the second treatment option (in this case, PTCA) relative to the predicted benefit of the first treatment option, TT (without the delay), and determines the amount of delay time for which randomization is acceptable, that is, the allowable delay time. Consequently, a given delay time for a second treatment option in excess of the allowable delay time results in a lesser benefit than that which would have been received if the first treatment option had been administered (without the delay). For such a given delay time, randomization is impermissible.

The processor module 16 uses logistic regression-based equations for computing the probability of mortality values. For further descriptions of predictive instruments which are capable of computing probabilities of ACI or other medical problems, reference may be had to the following patents: U.S. Pat. No. 4,957,115 by Selker, entitled "Device for Determining the Probability of Death of Cardiac Patients; U.S. Pat. No. 4,998,535 by Selker et al., entitled "Thrombolysis Predictive Instrument"; U.S. Pat. No. 5,277,188 by Selker, entitled "Clinical Information Reporting System"; and U.S. Pat. No. 5,501,229, U.S. Pat. No. 5,718,223 and U.S. Pat. No. 5,724,983, by Selker et al., and entitled "Continuous Monitoring Using a Predictive Instrument," all of which are incorporated herein by reference.

A logistic regression equation used by the predictive instrument is of the following form:

$$P=1/[1-\exp(-\Sigma\beta x)] \quad \text{Eq. (1)}$$

where P is the probability of a particular medical outcome or diagnosis, and where $\beta$ is the model coefficient, x is the variable value for the patient, and the sum is across all variables in the model. The variables x that are used in the model will of course depend upon the particular medical outcome or diagnosis which is being evaluated.

Standard, well-known regression techniques and other mathematical modeling may be employed to identify the most appropriate set of explanatory variables, and to determine the values of the coefficients of these variables. For a description of such techniques and examples of commercially available computer programs that implement them, see N. C. Cary in SUGI Supplement Library User's Guide, SAS Institute, p. 181–202, 1983, and L. Engelman, "PLR Stepwise Logistic Regression," BMDP Statistical Software, Chap. 14.5, pp. 330–334, BMDP publishers, Westwood, Calif. Of course, the precise set of explanatory variables that are identified and the predictive ability of the resulting logistic equation generally depends upon the quality of the underlying data that is used to develop the model. Such factors as the size and completeness of the database are often of significant importance. The selection of the relevant variables and the computation of the appropriate coefficients are well within the skill of an ordinary person skilled in the art.

Figure 2:
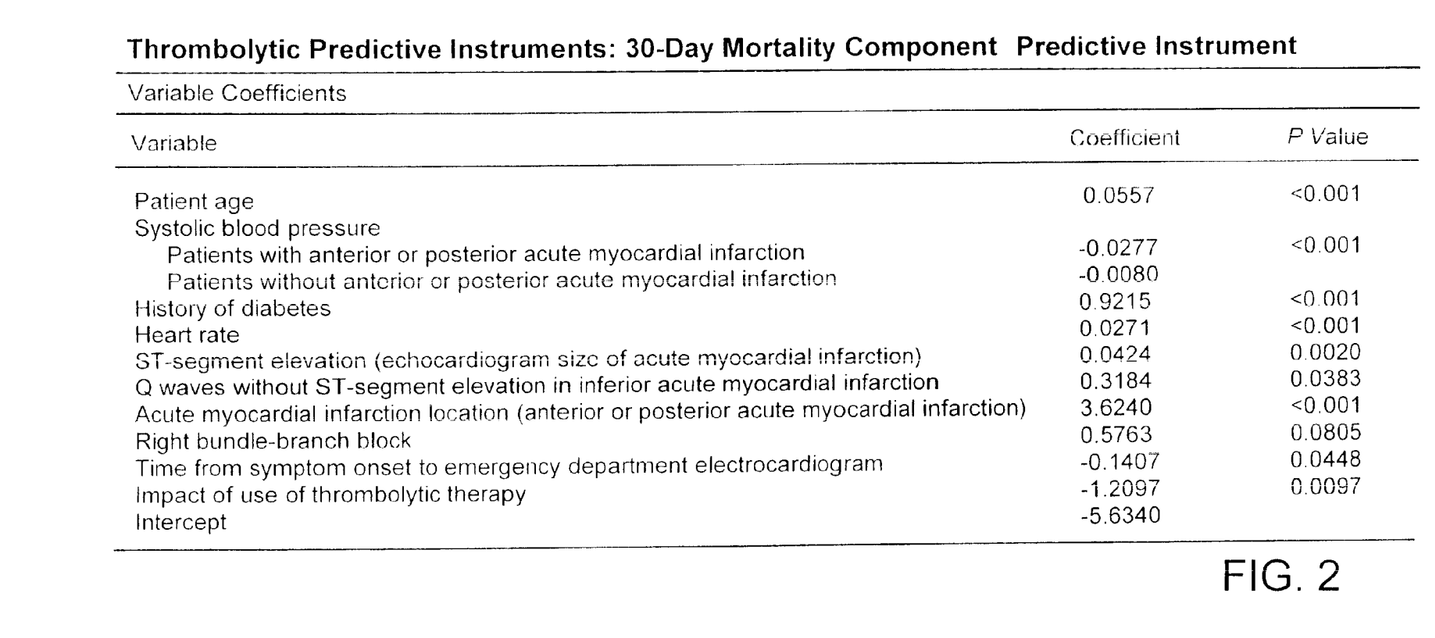
FIG. 2 presents the variables and coefficients of a logistic regression equation used to compute a prediction of mortality from myocardial infarction for treatment by thrombolysis therapy (TT)

Referring to FIG. 2, an exemplary set of variables and corresponding model coefficients to be included in Eq. (1) for calculating the probability of mortality (defined here as a 30-day mortality) with and without thrombolytic therapy treatment is shown. The illustrated variables were chosen as they represent clinical information commonly recorded for cardiac care patients considered for TT and were obtained using standard methods and materials. Note that one of the variables included in the TT model is "Impact of the use of TT", expressed in terms of "time (from symptom onset) to treatment", discussed above.

FIG. 3 illustrates a calculation for a sample patient using the Eq. (1) model for the probability of 30-day mortality with and without the administration of TT. For each variable in the model, the actual clinical data, the derived form needed for the calculations x, the variable coefficient $\beta$ and the weighted product $\beta*x$ are provided.

Although unstated in the Eq. (1) and FIGS. 2–3, it will be recognized that there is a variability or imprecision in the above-described calculation and that variability is typically expressed as an interval estimate referred to as a confidence interval. The confidence interval defines an upper limit and a lower limit associated with a particular level of probability, e.g., 95 percent. The confidence interval is a statistical confidence interval and is computed in known fashion from the confidence intervals implicit in the coefficients and parameters of the regression equation. The confidence interval, that is, the confidence level associated with the computed 30-day mortality prediction, will play a significant role in techniques employed by the randomization process, as discussed below.

It is important to note that the difference between the computed probabilities with and without treatment is a measure of predicted benefit, one that is used by the computations of the randomization process, as will now be described.

Figure 4A:
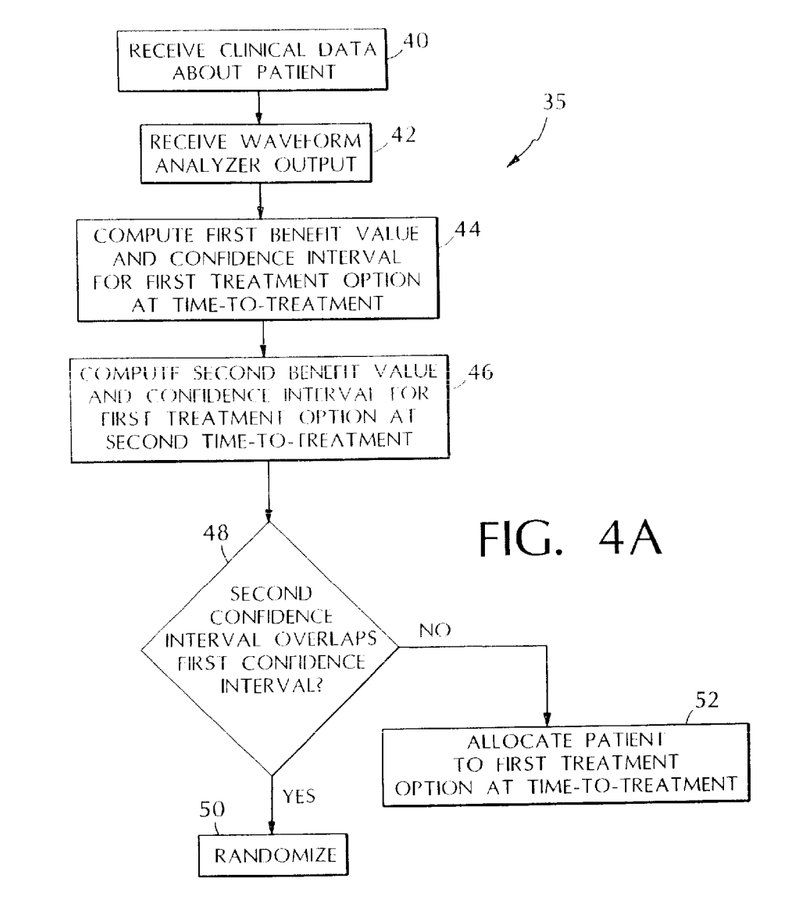
FIGS. 4A and 4B are flow diagrams of a patient randomization process performed by the predictive system of FIG. 1 for TT.
Figure 4B:
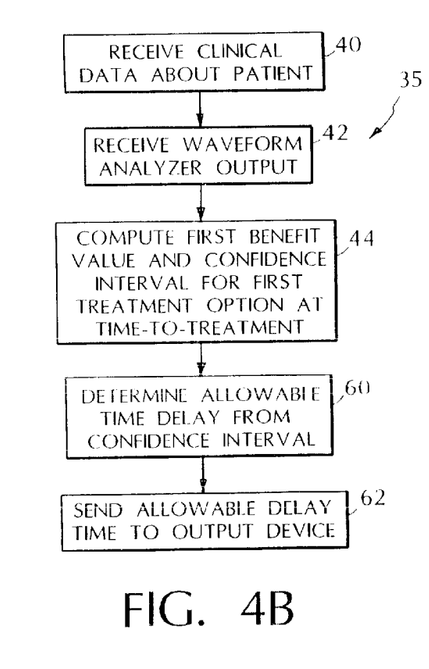
Figure 5:
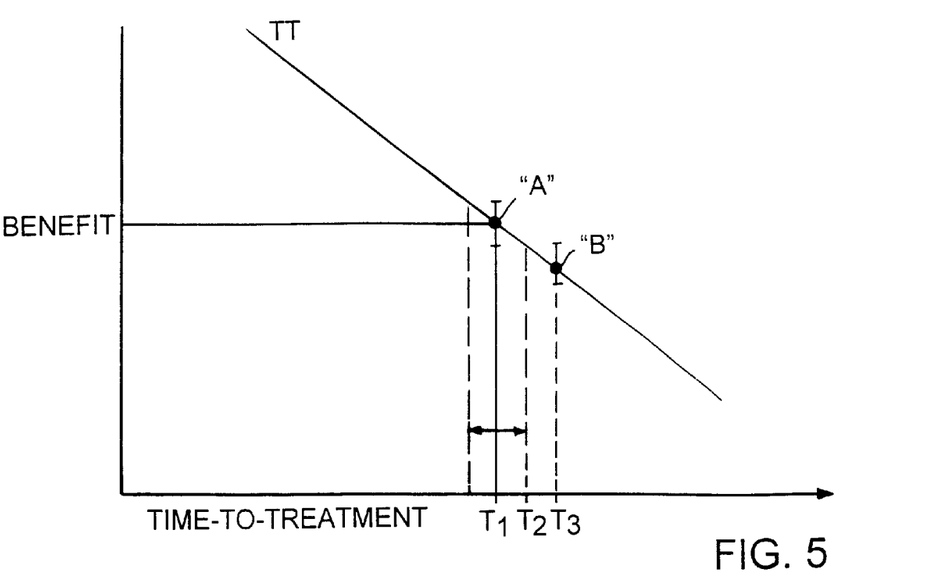
FIG. 5 is a graphical representation of benefit as a function of time-to-treatment for a treatment option such as Thrombolytic Therapy (TT)
Figure 6A:
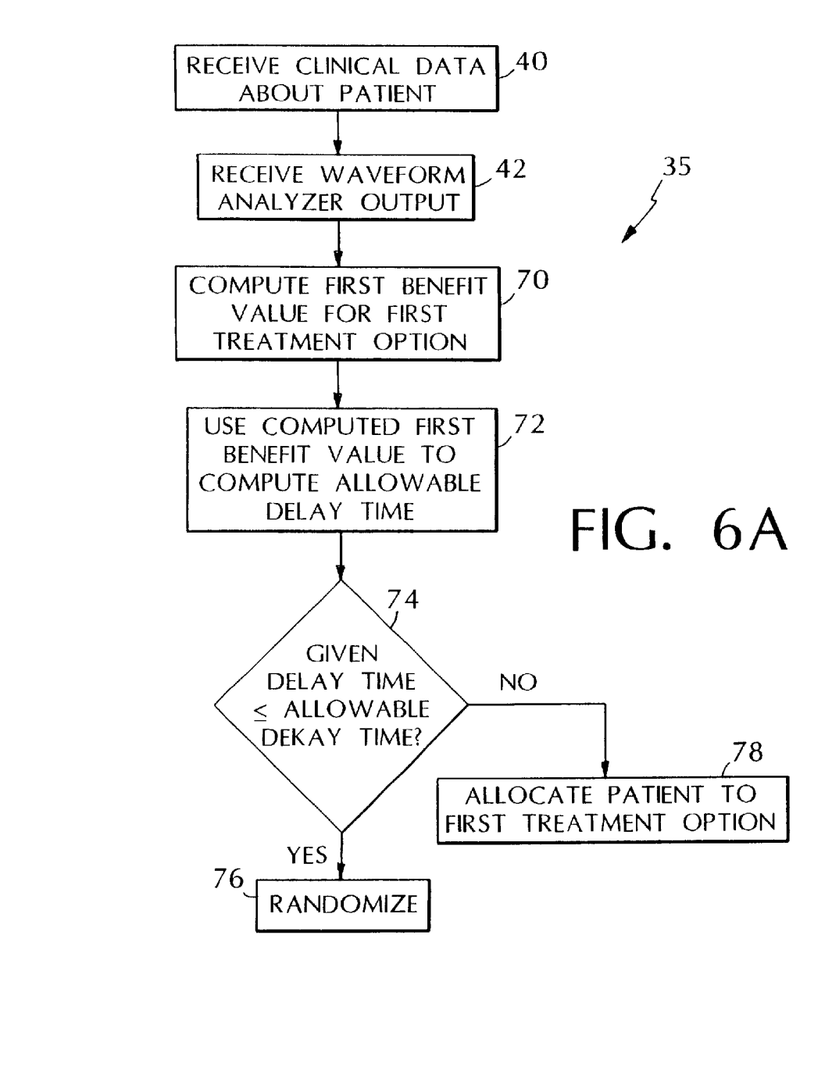
FIGS. 6A and 6B are flow diagrams of a patient randomization process performed by the predictive instrument of FIG. 1 for TT and an estimated PTCA.
Figure 6B:
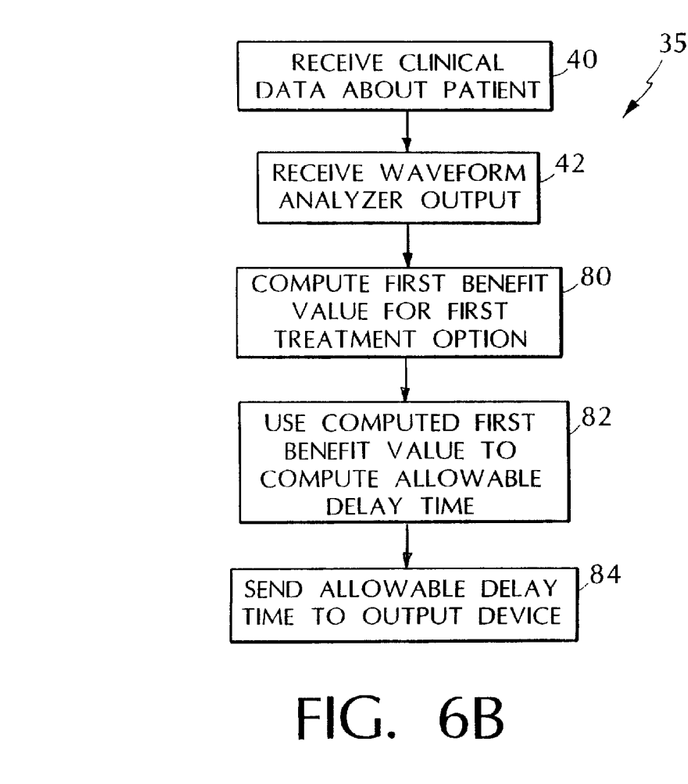
Figure 7:
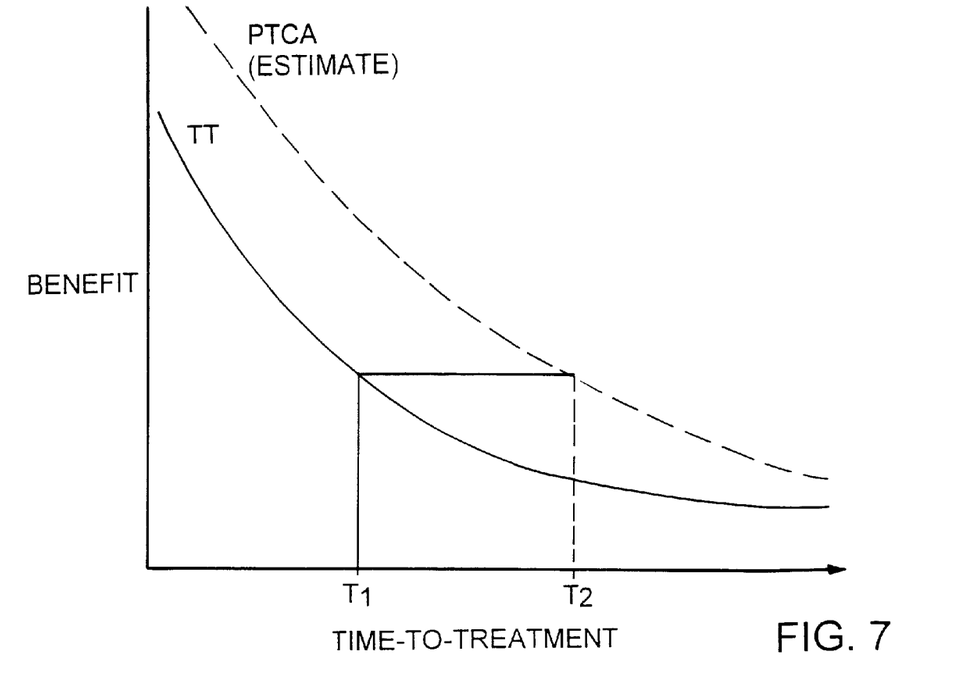
FIG. 7 is a graphical representation of benefit as a function of time-to-treatment for a first treatment option, TT, and an estimated benefit as a function of time-to-treatment for a second treatment option, PTCA.

As earlier mentioned, the randomization process 35 may involve at least two alternative treatment options. In the illustrate embodiment, the first treatment option, TT, is taken to be the standard of care. The process 35 may be used at different stages of an efficacy trial of the second treatment option, PTCA. At an early stage, little may be known about the benefits of the second treatment option. The data that exists might suggest that it is at least as good as, and possibly superior to, the first treatment option. At a later point, there may be preliminary clinical data to support an estimate of the benefit of the second treatment as some percentage greater than the first treatment option. As the trial progresses to a more advanced stage, a mathematical model for the second treatment option is developed and validated. Thus, the randomization process 35 is suitably adapted to the level of knowledge about the efficacy of the second treatment option. FIGS. 4–9 illustrate the process 35 as adapted for use at different stages of a PTCA efficacy trial. FIGS. 4A–B and 5 illustrate that stage in which little is known about the benefit of PTCA relative to TT except that the benefit of PTCA is at least equal to that of TT. FIGS. 6A–B and FIG. 7 illustrate the randomization process based on an estimated PTCA. In the process as illustrated in FIGS. 4A–4B and 6A–6B, a regression model exists for TT but not for PTCA.

Figure 8A:
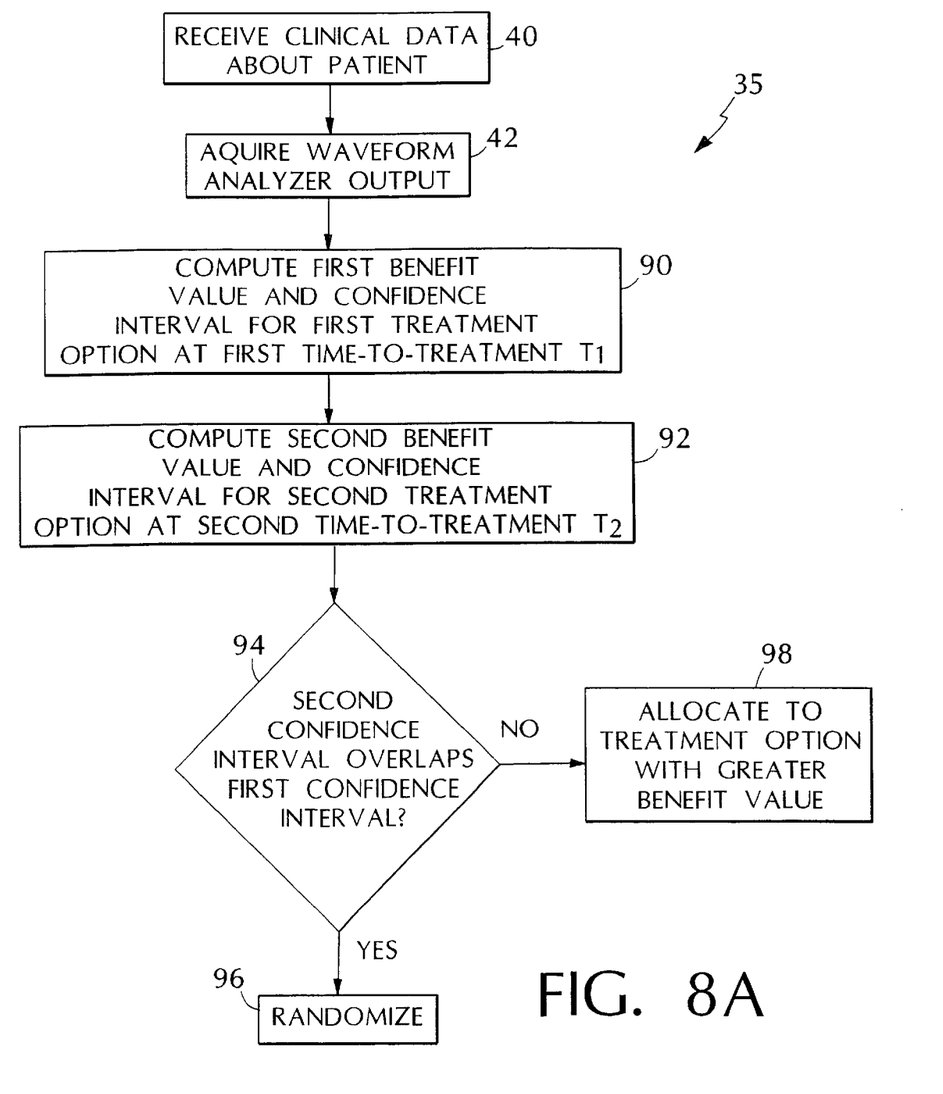
FIGS. 8A and 8B are flow diagrams of a patient randomization process performed by the predictive instrument of FIG. 1 for TT and PTCA.
Figure 8B:
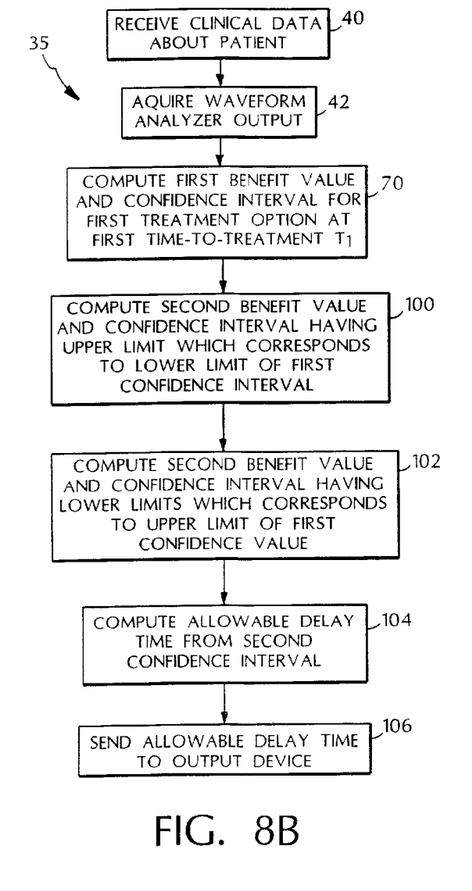
Figure 9:
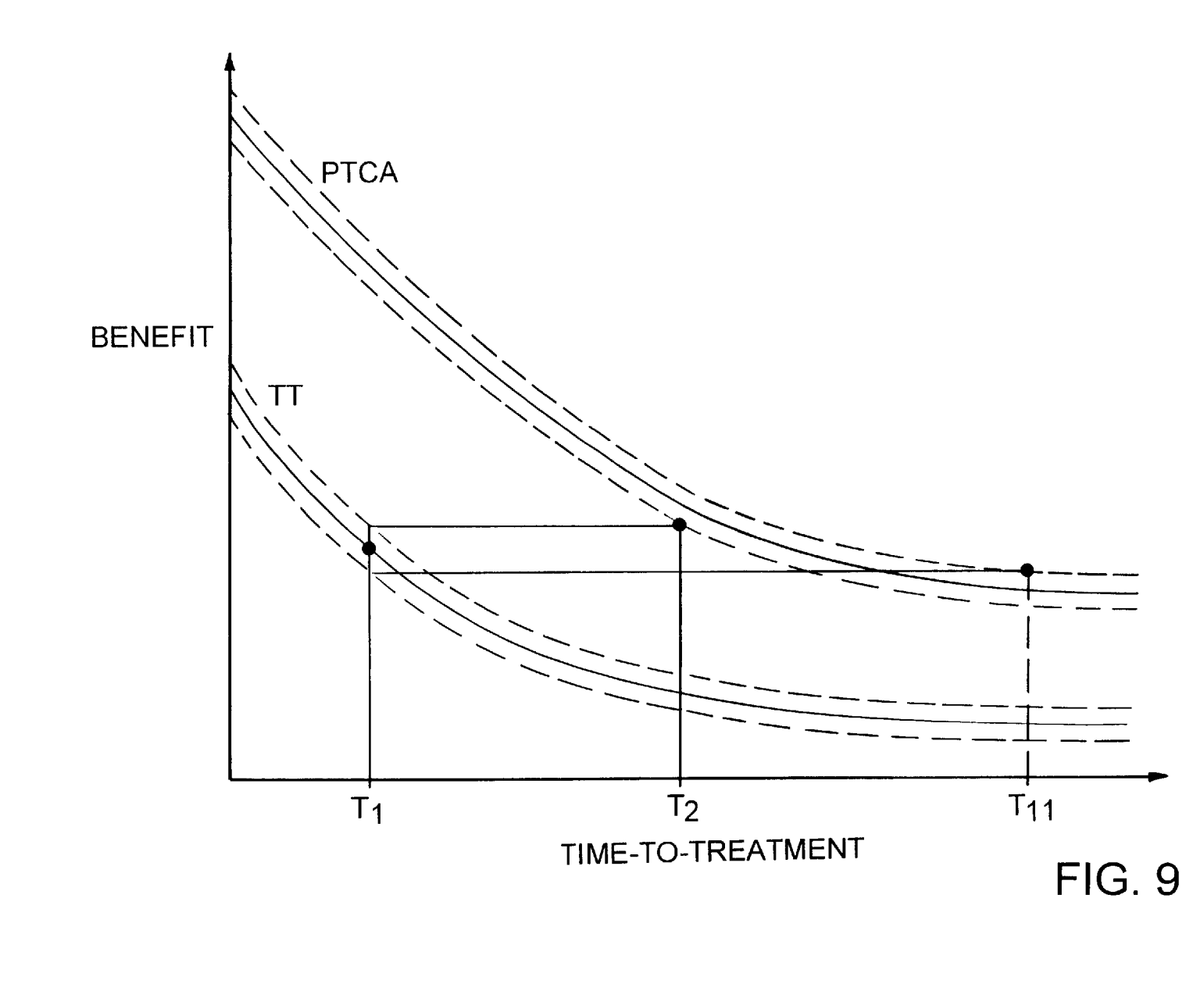
FIG. 9 is a graphical representation of benefit as a function of time-to-treatment for a first treatment option, TT, and a benefit as a function of time-to-treatment for a second treatment option, PTCA.

In FIGS. 8A–B and FIG. 9, the randomization process 35 assumes the existence of and thus employs regression models for both TT and PTCA.

Referring to FIG. 4A, the randomization process 35 is shown. As discussed above, it may be desirable to determine if a patient is a candidate for randomization, given an actual time delay to transport the patient to the hospital at which the second treatment option is available. Thus, the randomization process 35 determines the allowable delay time for which the benefit of the second treatment option at a delayed time-to-treatment is no less than that of the first treatment option at the first time-to-treatment.

Still referring to FIG. 4A, the randomization process 35 begins by receiving clinical data (step 40) and receiving the waveform analyzer output (step 42). In response to receiving the patient data and the waveform analyzer output, the process computes a first benefit value and a first confidence interval associated with the first benefit value for the first treatment option at the time-to-treatment (step 44). Given that there is little data available about the benefit associated with the second treatment option, but assuming that the benefit of the second treatment option is at least equal to the first treatment option, the process computes a second benefit value and an associated second confidence interval for the first treatment option at a second time-to-treatment time that is greater than the first time-to-treatment by the given delay time (step 46). Having computed the two benefit values and confidence intervals, the process determines if the second confidence interval overlaps the first confidence interval (step 48). If the process determines that the confidence intervals do indeed overlap, the process randomizes the patient to one of the treatment options, or, alternatively, indicates to the instrument user that randomization is possible with this patient (step 50). If the confidence intervals do not overlap, the process allocates the patient to the first treatment option at the first time-to-treatment, or signals to the user that the patient is not a suitable candidate for randomization (step 52).

In an alternative implementation, the process 35 does not signal to the user whether or not randomization may occur, but instead provides the allowable delay time information to the user. The user can then make the randomization determination based on the actual or given delay times of all available alternatives. Thus, with reference to FIG. 4B, the process performs the same steps 40, 42 and 44 as in FIG. 4A. At step 60, the process determines the allowable time delay from the confidence interval. The process sends the allowable time delay information to an output device, such as display 26 (step 62).

Referring to FIG. 5, a graphic representation of benefit over time for TT as the standard treatment option (the first treatment option) is shown. Using the confidence interval ("A") corresponding to the calculated benefit value for TT at $T_1$ (the time-to-treatment for TT), it can be appreciated that the allowable delay time corresponds to $T_2$ (the upper limit of the confidence interval "A") minus $T_1$; however, taking into account the confidence interval of a second treatment option ("B"), it can be seen that the allowable delay time actually corresponds to $T_3 - T_1$, as the confidence interval for an equivalent second treatment delayed in time will overlap the confidence interval of TT in the time interval bounded by $T_1$ and $T_3$.

Another embodiment, illustrated in FIGS. 6A–6B, instead of using confidence interval projections, computes an estimated PTCA benefit based on the TT benefit. It assumes that a limited amount of data relating to the efficacy of the second treatment option is known, i.e., PTCA is more effective than TT in reducing the probability of mortality (relative to no treatment) by some percentage. Current research data suggests that the percentage may be as great as 33. Therefore, the interval can be calculated from TT predictions as follows:

$$(P \text{ without } TT)T_1 - (P \text{ with } TT)T_1 = 1.33\{(P \text{ without } TT) T_2 - (P \text{ with } TT)T_2\} \quad \text{Eq. (2)}$$

The left side of Eq. (2) represents the predicted reduction in probability of mortality (i.e., benefit) of the use of TT at $T_1$. The right side of Eq. (2) represents the reduction in probability of mortality (i.e., benefit) of delayed PTCA at a time-to-treatment $T_2$. Thus, Eq. (3) may be expressed as follows:

$$(\text{benefit with } TT)T_1 = (\text{benefit with } PTCA)T_2 \quad \text{Eq. (3)}$$

Thus, in computing the time variable $T_2$, the method searches for that time in the future when the benefit of PTCA is estimated to be the same as the TT benefit value at $T_1$.

Referring now to FIG. 6A, the randomization process 35 for predicted TT and an estimated PTCA is shown. The data acquisition is the same as was earlier described in steps 40–42 of FIGS. 4A and 4B. In this embodiment, the process computes the first benefit value (step 70) and uses the computed first benefit value at the first time-to-treatment to compute an allowable delay time within which a benefit value for the second treatment option is no less than the computed first treatment option (step 72). That is, it computes $T_2 - T_1$. The process 35 compares a given delay time (of the second treatment) option to the allowable delay time to determine if the given delay time is less than or equal to the allowable delay time (step 74). If the given delay time is less than or equal to the allowable delay time, the process 35 randomizes the patient or indicates to the user that randomization may occur (step 76). Otherwise, the process 35 allocates the patient to the first treatment option or indicates that the patient is ineligible for randomization (step 78). Thus, in steps 74–78, the process produces randomization information, in this case, an indication of whether or not randomization is acceptable, based on the allowable delay time.

Alternatively, as shown in FIG. 6B, producing randomization information includes communicating the allowable delay time to the user for use in randomization. That is, the process computes the first benefit value (step 80) and uses the computed first benefit value at the first time-to-treatment to compute the allowable delay time within which the benefit value for the second treatment option is no less than that computed for the first treatment option (step 82). The process sends the allowable delay time information to an output device for display (step 84).

FIG. 7 is a graphic representation of benefit over time for the randomization process 35 of FIGS. 6A–6B. As shown in the graph, time period $T_2-T_1$ is the time interval extending from the time-to-treatment for TT ($T_1$) until that future time-to-treatment for PTCA ($T_2$)—or, the allowable delay time as discussed above. The point $T_2$ is the point in time at which the predicted mortality for PTCA is equivalent to that of TT.

Although the model of FIGS. 6–7 is based on an estimated PTCA, it will be appreciated that, given a dataset of variables and outcomes (such as those obtained from a randomized clinical trial employing the randomization technique described in FIG. 7), a logistic regression equation could be derived for PTCA. If the PTCA equation includes the same time variable as TT (i.e., time-to-treatment), it would be possible to compute a predicted outcome for PTCA in the same manner as described above with reference to TT. Mathematical models of TT and PTCA could then be used to define the allowable delay time in a more precise manner, as described below.

Therefore, in yet another embodiment, and as illustrated in FIG. 8A, the patient randomization process 35 employs regression models of both TT and PTCA. The process 35 receives clinical patient data (step 40) and acquires the wavelength analyzer output (step 42). The process computes a first benefit value and an associated first confidence interval for a first treatment option (TT) at a first time-to-treatment $T_1$, (step 90). The process further computes a second benefit value having an associated second confidence interval for a second treatment option (PTCA) at a delayed time-to-treatment $T_2$ (step 92). The process compares the computed confidence intervals to determine if the second confidence interval overlaps the first confidence interval (step 94). If the process determines that an overlap exists, it randomizes the patient to one of the treatment options (step 96). If the second confidence interval does not overlap the first confidence interval, the process selects the appropriate treatment option (step 98). That is, it compares the benefit values and selects the treatment option which yields the greater benefit at its respective time-to-treatment.

As was described previously with reference to FIGS. 6B and 7B, the process may be used to determine the allowable delay time for randomization as an output. Thus, the process still performs steps 40, 42 and 70 as described above with reference to FIG. 8A. However, the second time-to-treatment may not be known or there may be several more distant hospitals to choose from. Thus, the user of the predictive instrument 10 may simply wish to know the allowable delay time in which randomization may occur. The process computes a second benefit value and confidence interval having an upper limit ("second upper limit" or $T_U$) corresponding to the lower limit of the computed confidence interval of the first treatment option (step 100). The process 35 also computes the second benefit value and confidence interval having a lower limit ("second lower limit" or $T_L$) corresponding to the upper limit of the confidence interval of the first treatment option (step 102). From the second upper and lower limits the process computes the allowable delay time in terms of a minimum allowable delay time $T_L-T_1$ and a maximum allowable delay time $T_U-T_1$ (step 104). The process 35 sends the computed allowable delay time information to an output device for display (step 106).

Referring now to FIG. 9, a graphical representation for benefit over time using a refined computation based on mathematical models of both TT and PTCA (i.e., the benefit computations of FIGS. 8A and 8B) is shown. Taking into account the confidence intervals inherent in the probability of mortality calculations for both treatment options, it can be appreciated that the allowable delay time is defined over a region in which the confidence interval for PTCA overlaps the confidence interval of TT at the time-to-treatment $T_1$-that is, $T_L$(lower limit) to $T_U$(upper limit). Thus, if the delayed time-to-treatment $T_2$ for PTCA falls within this region $T_L$-to-$T_U$, the patient can be randomly allocated to either TT or PTCA. A $T_2$ that is within the range of $T_1$-to-$T_L$, however, clearly mandates the use of PTCA. Conversely, for a $T_2 > T_U$, TT (at $T_1$) is the appropriate treatment option. In terms of delay time, a given delay time $T_2-T_1$ cannot be less than the minimum allowable delay time $T_L-T_1$ or greater than the maximum allowable delay time $T_U-T_1$.

In the embodiments described above, the processor module outputs randomization information in the form an allowable By time delay for randomization or a randomization assignment. It will be understood that, in any of the above embodiments, the randomization information which is returned to the user of the predictive instrument could take other forms, e.g., an actual time interval (i.e., the bounds of the delay time); an indicator indicating that randomization is acceptable or unacceptable; and so forth. The processor module outputs the randomization information in a form and manner that is designed to be most useful to the physician or care provider using the instrument.

Figure 10:
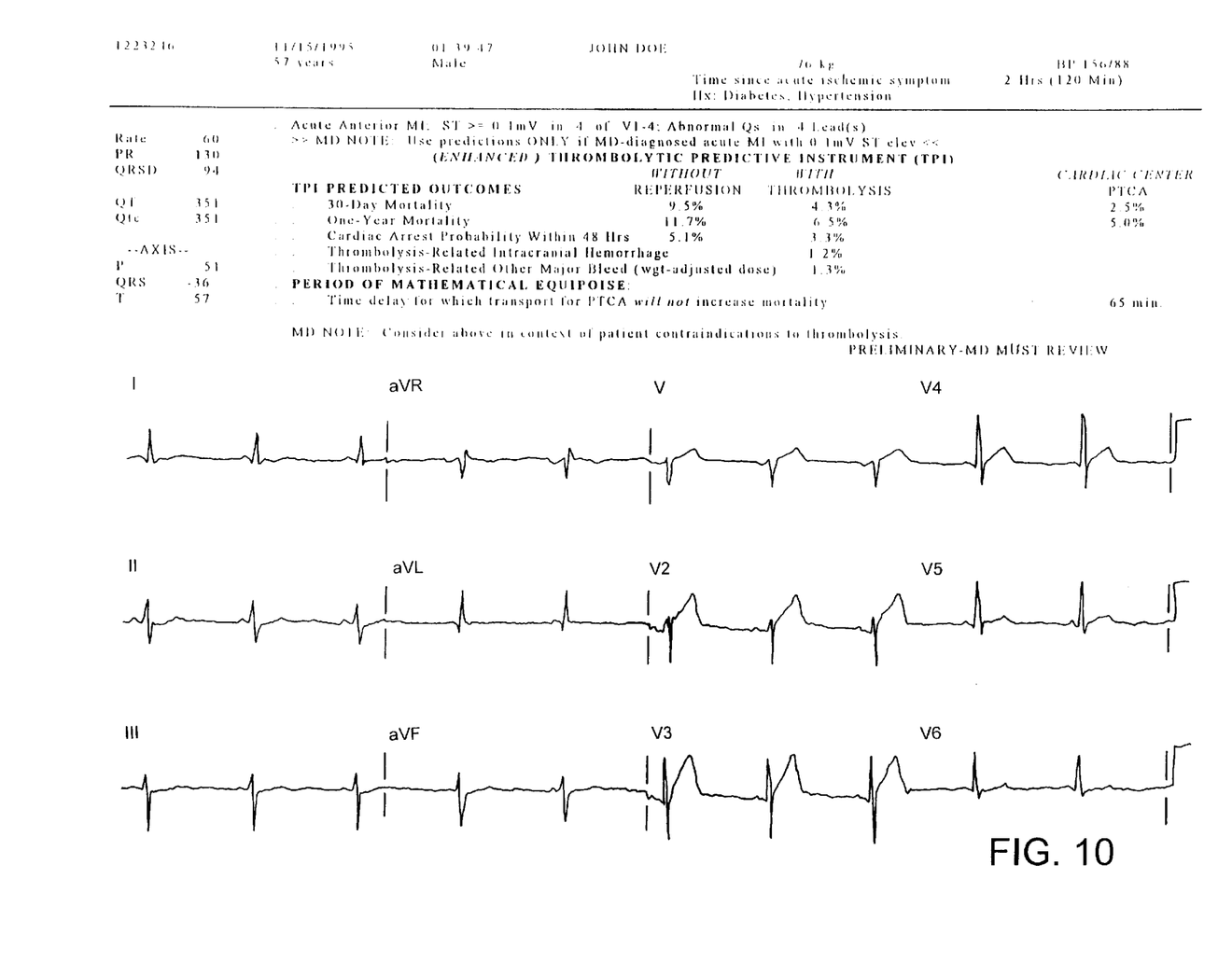
FIG. 10 is an example of a printout from the predictive instrument of FIG. 1.

Referring to FIG. 10, an exemplary printout is shown. In this example, the printer 22 (FIG. 1) prints the results across the top of the ECG waveform trace output that is generated by the electrocardiograph so that a permanent record of them is generated for the patient's file and so that they are available in a convenient readily accessible form. Alternatively, or in addition, the results can be displayed in some other fashion such as through the display 26 (FIG. 1).

The significance of the information which is communicated to the physician or other care provider (e.g., EMS personnel) in the example shown in FIG. 10 is as follows. In the example shown, the ECG of a 57 year old male indicates the 30 day mortality for the following scenarios: 1) the patient receives no reperfusion therapy; 2) the patient receives thrombolysis; and 3) the patient is brought to a cardiac center and receives PTCA. Based upon the monitored ECG waveform and the presenting information that is obtained from the patient, the printout indicates that the computed probability of 30-day mortality without reperfusion is 9.5% and is 4.3% for TT. The printout also indicates that the "estimated" probability of 30-day mortality for PTCA administered at a cardiac center is 2.5%. The ECG header further specifies that, for these computed mortality values relative to the computed value without reperfusion (9.5%), the maximum PTCA time delay (e.g., transport delay) which will not increase mortality, i.e., the allowable delay time, is 65 minutes. Thus, if an EMS care provider in a field setting is facing a choice between sending a patient to TT at a local hospital only a few minutes away or PTCA at a cardiac center that is an additional 30 minutes away, the randomization information provided by the ECG header would indicate to that provider that the additional 30 minutes of transport time to obtain PTCA is within the allowable delay time and is therefore permissible. Consequently, this particular patient may be randomized, as the benefit of the delayed PTCA treatment will be no less than the benefit of TT at the earlier time.

In still yet another embodiment, the concept of patient randomization may be extended to other applications which do not involve a time-to-treatment variable. One example of such an application would be a clinical trial for experimental drug testing.

Figure 11:
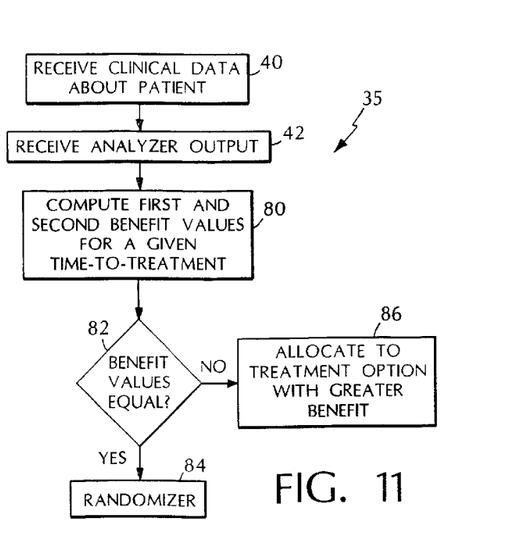
FIG. 11 is a flow diagram of an alternative patient randomization operation performed by the predictive instrument of FIG. 1.

Referring to FIG. 11, a randomization process 35' is shown. The process receives clinical data input (step 40) and receives the output of a patient monitoring device (step 42). The randomization process 35' computes a first benefit value and a second benefit value (step 80). The process 35' compares the computed benefit values to determine if the two compared benefit values are equal (step 82). If the two values are equal, the process randomizes the patient (step 84). Otherwise, the patient is allocated to the appropriate treatment option (e.g., drug treatment) with the greater computed benefit value (step 86). As discussed above, the equivalency of the benefit values may be determined through the use of their associated confidence intervals. If the confidence intervals overlap, the two treatments are treated as providing the same benefit.

While the embodiments presented above illustrate how the invention can be used to enable the random allocation of patients to specific treatment options within the realm of cardiac care, the invention is not so limited.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining if a patient qualifies to be randomized to
   a treatment option, the method comprising:
      receiving data fur a patient experiencing symptoms of the type that are amenable to being treated by either of two treatment options including a first treatment option having a first time-to-treatment and at second treatment option having a second time-to-treatment that is greater than the first time to treatment by a given delay time, the second treatment option estimated to be more effective than the first treatment option;
   using the received data to compute for the first treatment option at the first time-to-treatment a benefit value,
   using the received data and the computed benefit value associated with the first treatment option to compute for the second treatment option a allowable delay time during which a second benefit value for the second treatment option is no less than the first benefit value; and
   producing randomization information to indicate whether or not the patient qualifies to be randomized to one of the two treatment options based on the computed allowable delay time.

2. The method of claim 1, wherein producing randomization information comprises:
   determining if the given delay time is less than or equal to the allowable delay time; and indicating that the patient qualifies to be randomly allocated to either the first or the second treatment option if the given delay time is determined to be less than or equal to the allowable delay time.

3. The method of claim 1, wherein producing randomization information comprises:
   sending the computed allowable delay time to an output device for display.

4. The method of claim 1, wherein the first treatment option is thrombolytic therapy.

5. The method of claim 1, wherein the second treatment option is percutaneous transluminal coronary angioplasty.

6. The method of claim 1, wherein the first treatment option is available at a local hospital, the second treatment option is available at a referral care center and the given time delay is a patient transport time delay.

7. A method of determining if a patient qualifies to be randomized to a treatment option, the method comprising:
   receiving data for a patient experiencing symptoms of the type that are amenable to being treated by either of two treatment options including a first treatment option having a first time-to-treatment and a second treatment option having a second time-to-treatment that is greater than the first time to treatment, the second treatment option being at least as effective as the first medical treatment option;
   using the received data to compute for the first treatment option at the first time-to-treatment a first benefit value, the first benefit value having a first confidence interval associated therewith;
   using the received data to compute for the first treatment option at a time equal to the second time to treatment a second benefit value, the second benefit value having a second confidence interval associated therewith;
   determining if the second confidence interval overlaps the first confidence interval; and
   indicating that the patient qualifies to be randomly allocated to either the first or the second treatment option if the second confidence interval is determined to overlap the first confidence interval.

8. A method of determining if a patient qualifies to be randomized to a treatment option, the method comprising:
   receiving data for a patient experiencing symptoms of the type that are amenable to being treated by either of two treatment options including a first treatment option having a first time-to-treatment and a second treatment option having a second time-treatment that is greater than the first time to treatment by a given delay time, the second treatment option assumed to be at least as effective as the first medical treatment option;
   using the received data to compute for the first treatment option at the first time-to-treatment a benefit value, the benefit value having a confidence interval associated therewith;
   determining from the confidence interval an allowable delay time;
   determining if the given delay time is less than or equal to the allowable delay time; and
   indicating that the patient qualifies to be randomly allocated to either the first or the second treatment option if the given delay time is determined to be less than or equal to the allowable delay time.

9. A method of determining if a patient qualifies to be randomized to a treatment option, the method comprising:
   receiving data for a patient experiencing symptoms of the type that are amenable to being treated by either of two treatment options including a first treatment option having a first time-to-treatment and second treatment option having a second time-to-treatment that is greater than the first time to being treatment, the second treatment option more effective than the first treatment option;
   using the received data to compute for the first treatment option at the first time-to-treatment a first benefit value, the first benefit value having a first confidence interval associated therewith;
   using the received data for the preferred second medical treatment option at the second time-to-treatment a second benefit value, the second benefit value having second confidence interval associated therewith;
   determining if the second confidence interval overlaps the first confidence interval; and
   indicating that the patient qualifies to be randomly allocated to either the first or the second treatment option if the second confidence interval is determined to overlap the first confidence interval.

10. A method of determining if a patient qualifies to be randomized to a treatment option, the method comprising:
    receiving data for a patient experiencing symptoms of the type that are amenable to being treated by either of two treatment options including a first treatment option having a first time-to-treatment and a second treatment option having a second time-to-treatment that is greater than the first time to treatment by a given delay time, the second treatment option being more effective than the first treatment option;

using the received data to compute for the first medical treatment option at the first time-to-treatment a benefit value, the benefit value having a confidence interval associated therewith;

using the received data to compute benefit values as a function of time for the preferred second medical treatment option, each of the benefit values having confidence intervals associated therewith;

defining an allowable time delay for which the confidence interval associated with the computed benefit value for the first treatment option overlaps the confidence intervals associated with computed benefit values for the second treatment option, thereby determining those of the computed benefit values which are equal to the computed benefit value for the first medical treatment option;

determining if the given time delay is within the less than or equal to the allowable time delay; and indicating that the patient qualifies to be randomly allocated to either the first or the second treatment option if the given delay time is determined to be less than or equal to the allowable delay time.

11. A method of determining if a patient qualifies to be randomized to a treatment option, comprising:

receiving data for a patient experiencing symptoms of the type that are amenable to being treated by either of two treatment options including a first treatment option and second treatment option;

computing a first probability of medical outcome value for the first treatment option using the received data;

computing a second probability of medical outcome value for the second treatment option using the received data;

determining if the first and second computed probability of medical outcome values are equal; and indicating that the patient qualifies to be randomly allocated to either the first or the second treatment option if it is determined that the first and second computed probability of medical outcome values are equal.

12. A computer program residing on a computer-readable medium for determining if a patient qualifies to be randomly allocated to a treatment option, the computer program comprising instructions causing a computer system to:

receive data for a patient experiencing symptoms of the type that are amenable to being treated by either of two treatment options including a first treatment option having a first time-to-treatment and a second medical treatment option having a second time-to-treatment that is greater than the first time-to-treatment by a given delay time, the second treatment option estimated to be more effective than the first treatment option;

use the received data to compute for the first treatment option at the first time-to-treatment a benefit value;

use the received data and the computed benefit value associated with the first treatment option to compute for the second treatment option an allowable delay time during which a second benefit value for the second treatment option is no less than the first benefit value; and produce randomization information to indicate whether or not the patient qualifies to be randomized to one of the two treatment options based on the computed allowable delay time.

13. The computer program of claim 12, wherein the instructions causing the computer to produce randomization information comprise instructions causing the computer to:

determine if the given delay time is less than or equal to the allowable delay time; and indicate that the patient qualifies to be randomly allocated to either the first or the second treatment option if the given delay time is determined to be less than or equal to the allowable delay time.

14. The computer program of claim 12, wherein the instructions causing the computer to produce randomization information comprise instructions causing the computer to:

send the computed allowable delay time to an output device for display.

15. A computer program residing on a computer-readable medium for determining if a patient qualifies to be randomly allocated to a treatment option, the computer program comprising instructions causing a computer system to:

receive data for a patient experiencing symptoms of the type that are amenable to being treated by either or two treatment options including a first treatment option having a first time-to-treatment and a second treatment option having a time to treatment that is greater than the first time-to-treatment, the second treatment option being at least as effective as the first treatment option;

use the received data to compute for the first treatment option at the first time-to-treatment a first benefit value, the first benefit value having a first confidence interval associated therewith;

use the received data to compute for the first treatment option at a time equal to the second time-to-treatment a second benefit value, the second benefit value having a second confidence interval associated therewith;

determine if the second confidence interval overlaps the first confidence interval; and indicate that the patient qualifies to be randomly allocated to either the first or the second treatment option if the second confidence interval is determined to overlap the first confidence interval.

16. A computer program residing on a computer-readable medium for determining if a patient qualifies to be randomly allocated to a treatment option, the computer program comprising instructions causing a computer system to:

receive data for a patient experiencing symptoms of the type that are amenable to being treated by either of two treatment options including a first treatment option having a first time-to-treatment and second treatment option having a second time-to-treatment that is greater than the first time-to treatment, the second treatment option being more effective than the first treatment option;

use the received data to compute for the first treatment option at the first time-to-treatment a first benefit value, the first benefit value having a first confidence interval associated therewith;

use the received data for the preferred second treatment option at the second presentation time a second benefit value, the second benefit value having second confidence interval associated therewith;

determine if the second confidence interval overlaps the first confidence interval; and indicate that the patient qualifies to be randomly allocated to either the first or the second treatment option if the second confidence interval is determined to overlap the first confidence interval.

17. A computer program residing on a computer-readable medium for determining if a patient qualifies to be randomly allocated to a medical treatment option, the computer program comprising instructions causing a computer system to:

receive data for a patient experiencing symptoms of the type that are amendable to being treated by either of two treatment options including a first treatment option and second treatment option;

compute a first probability of medical outcome value for the first treatment option using the received data;

compute a second probability of medical outcome value for the second treatment option using the received data;

determine if the first and second computed probability of medical outcome values are equal; and indicate that the patient qualifies to be randomly allocated to either the first or the second treatment option if it is determined that the first and second computed probability of medical outcome values are equal.

* * * * *

UNITED STATES PATENT AND TRADEMARK OFFICE
CERTIFICATE OF CORRECTION

PATENT NO.    : 6,450,954 B1
DATED         : September 17, 2002
INVENTOR(S)   : Harry P. Selker

It is certified that error appears in the above-identified patent and that said Letters Patent is hereby corrected as shown below:

<u>Column 11,</u>
Line 19, "first time-to-treatment and at second" should be -- first time-to-treatment and a second --.

<u>Column 14,</u>
Line 21, "amenable to being teated by either or two" should be -- amenable to being treated by either of two --.

Signed and Sealed this

Fourth Day of February, 2003

JAMES E. ROGAN
*Director of the United States Patent and Trademark Office*